United States Patent [19]
Karlin et al.

[11] Patent Number: 4,583,539
[45] Date of Patent: Apr. 22, 1986

[54] LASER SURGICAL SYSTEM

[75] Inventors: David B. Karlin, New York, N.Y.;
Chandra K. N. Patel, Summit, N.J.;
Obert R. Wood, II, New York, N.Y.;
Thomas J. Bridges, Holmdel, N.J.;
Albert R. Strnad, Colts Neck, N.J.

[73] Assignees: Cornell Research Foundation, Inc., Ithaca, N.Y.; Bell Telephone Laboratories, Inc., Murray Hill, N.J.

[21] Appl. No.: 338,926

[22] Filed: Jan. 12, 1982

[51] Int. Cl.⁴ .............................................. A61B 17/36
[52] U.S. Cl. ..................... 128/303.1; 128/395; 219/121 LQ; 350/96.32
[58] Field of Search ..................... 128/303.1, 395–398; 219/121 L, 121 LR, 121 LQ, 121 LP, 121 LZ; 372/108; 350/96.32

[56] References Cited

U.S. PATENT DOCUMENTS

| | | | |
|---|---|---|---|
| 3,386,043 | 5/1968 | Marcatili et al. | 330/4.3 |
| 3,481,340 | 12/1969 | McKnight et al. | 128/395 |
| 3,658,406 | 4/1972 | Karube et al. | 350/52 |
| 3,703,176 | 11/1972 | Vassiliadis et al. | 128/303.1 X |
| 3,913,582 | 10/1975 | Sharon | 128/303.1 |
| 3,982,541 | 9/1976 | L'Esperance, Jr. | 128/303.1 |
| 4,120,293 | 10/1978 | Muckerheide | 128/395 X |
| 4,122,853 | 10/1978 | Smith | 128/303.1 |
| 4,123,143 | 10/1978 | Yachin et al. | 128/303.1 |
| 4,170,997 | 10/1979 | Pinnow et al. | 128/395 |
| 4,266,548 | 5/1981 | Davi | 128/303.1 |
| 4,309,998 | 1/1982 | Aron | 128/303.1 |
| 4,473,074 | 9/1984 | Vassiliadis | 128/303.1 |

FOREIGN PATENT DOCUMENTS

| | | | |
|---|---|---|---|
| 2700452 | 7/1977 | Fed. Rep. of Germany | 128/303.1 |
| 77989 | 6/1980 | Japan | 219/121 LZ |

OTHER PUBLICATIONS

Gamire et al., "Low-Loss Propagation . . . Waveguides", Appl. Phys. Lett., 34(1), Jan. 1979, pp. 35–37.
Bridges et al., "Single Crystal AgBr . . . ", Optics Letters, vol. 5, No. 3, pp. 85–86, Mar. 1980.
Pinnow et al., "Polycrystalline Fiber Optical Waveguides . . . ", Appl. Phys. Lett., 33(1), pp. 28–29, Jul. 1978.
Hikada et al., "Hollow-core Oxide-Glass Cladding . . . ", J. Appl. Phys., 52(7), pp. 4467–4471, Jul. 1981.
Marcatili et al., "Hollow Metallic and Dielectric . . . ", The Bell System Tech. Journal, pp. 1783–1809, Jul. 1964.
Smith, "A Waveguide Gas Laser", Appl. Phys. Lett., vol. 19, No. 5, pp. 132–134, Sep. 1971.
McMahon et al., "Waveguides For . . . Lasers", Technical Paper.

*Primary Examiner*—Lee S. Cohen
*Attorney, Agent, or Firm*—Sughrue, Mion, Zinn, Macpeak, and Seas

[57] ABSTRACT

A laser surgical instrument uses a $CO_2$ laser source and an articulated arm structure to maintain single mode transmission of a 10.6 $\mu$m beam to probe. In one configuration, high power is maintained for photo-transection and/or photocauterization. A second probe embodiment introduces other degrees of functionality such as aspiration, irrigation and internal viewing. Internal illumination is achieved by using the sheaths of quartz waveguides to transmit visible light while the laser beam is propagated internally in the waveguide structure.

25 Claims, 7 Drawing Figures

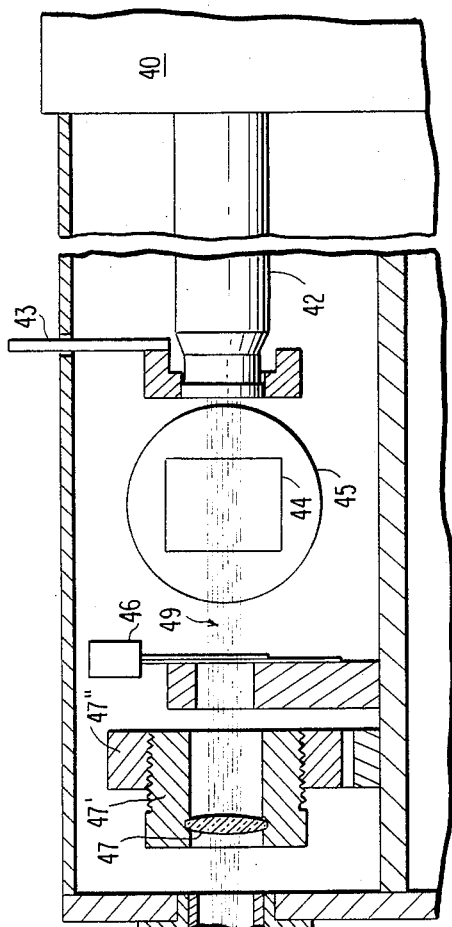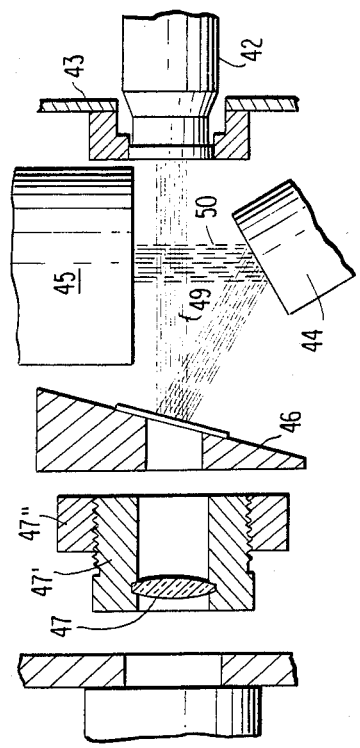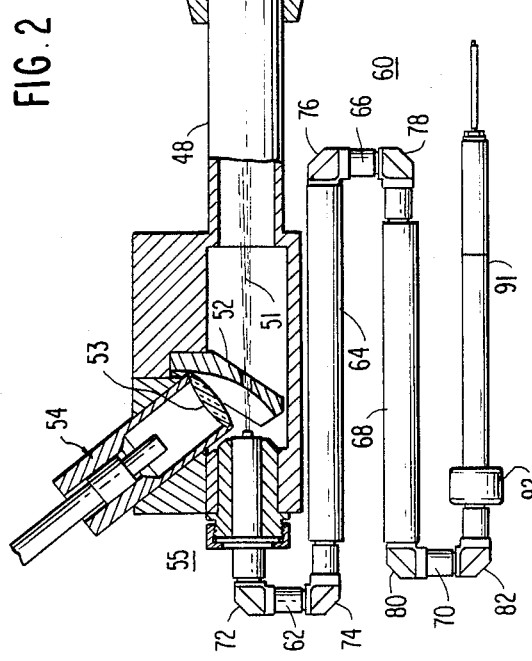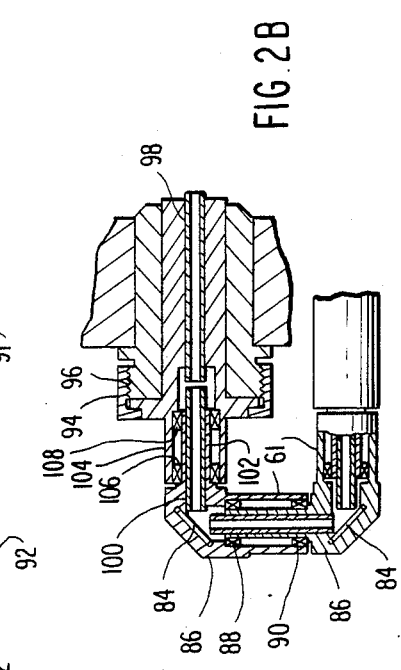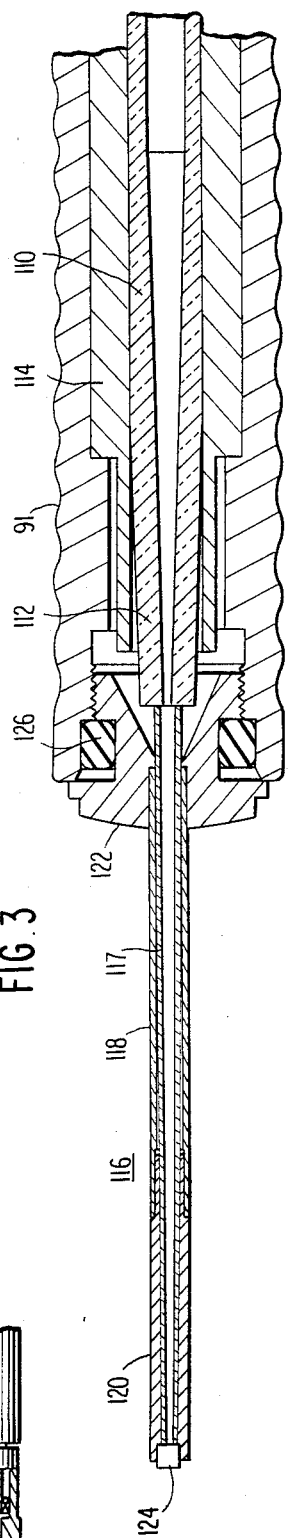

LASER SURGICAL SYSTEM

BACKGROUND OF THE INVENTION

This invention relates generally to intravitreal surgical techniques utilizing the direct application of a laser beam into the vitreous cavity. In particular, this invention relates to the use of a surgical instrument for vitreous surgery employing a $CO_2$ laser probe incorporating illumination of and viewing from within the eye. This surgical instrument also includes the capability of aspiration for removal of vitreous material together with the maintenance of intraocular pressure by means of irrigation.

This invention is related to a co-pending application entitled "Articulated Arm Radiation Guide" filed by T. J. Bridges and A. R. Strnad on the same day as this application, Ser. No. 338,871.

The prior art is replete with a number of concepts together with reports in the scientific literature evidencing limited instances of actual use of a $CO_2$ laser in ophthamalic procedures. The use of lasers as surgical tools, and in particular, $CO_2$ laser systems to accomplish simultaneous cutting and cauterization, is now well established. Cutting action, a result of intense local heating of the tissue due to absorption, occurs when the focused laser beam impinges on the tissue. Cauterization occurs simultaneously due to heating. The beam's energy is absorbed by the medium and will not propagate through it.

The use of a $CO_2$ laser, operating at 10.6 μm wavelength, offers both advantages and disadvantages in surgical procedures. $CO_2$ lasers have been particularly useful for the treatment of biological tissue reached by surface application of the radiation directly onto the area affected. Typical uses are dermatological, laryngological and gynecological polyp excisions. The use of a $CO_2$ laser for the treatment of tissue located within an absorbing medium has, however, to date been generally unsuccessful. This is because the laser radiation at 10.6 μm is completely absorbed by the fluid or tissue that it first impinges. That is, the beam will not penetrate through layers of tissue without first vaporizing or damaging those outer layers. It is for this reason that $CO_2$ laser techniques have heretofore found application in surface procedures.

The characteristic of complete absorption of the $CO_2$ laser beam's energy does however find unique application in vitreous surgery. This microsurgery poses requirements for exact cutting of vitreoretinal membranes and elimination of hemorrhage in situ at a precise point within the spherical vitreous cavity. Present intravitreal techniques for the removal of vitreous hemorrhage and cutting vitreoretinal adhesions have utilized two approaches for entry into the vitreous cavity. One, transcorneal, utilizes a corneoscleral incision and the removal of the crystalline lens. The second, trans pars plana, utilizes an instrument which is inserted through the ocular coates, at a point behind the lens. Following removal of hemorrhagic vitreous and reattachment of the retina, the vitreous cavity is, where necessary, filled with normal saline, human vitreous or other suitable fluid such as Ringers. Vitreous surgery utilizes mechanical cutters and suction probes to remove vitreous hemorrhage and/or cut vitreoretinal membranes. Existing surgery frequently requires manipulation of the vitreoretinal bands resulting in secondary vitreous hemorrhage. The technique is performed utilizing an operating microscope or indirect ophthalmoscope.

The two techniques referred to above have traditionally utilized various mechanical cutting instruments. Vitrectomy instruments currently in actual use are conventionally either motor, air or solenoid driven. Rotary, oscillatory or guillotine-like cutters have been developed. The essential concept of each is cutting and removal of the vitreous material from the eye with suction and the replacement of aspirated vitreous with infusion fluid. A hallmark deficiency of such mechanical cutting is that the opening is not at the tip of the probe and thus cutting action is limited when operations take place close to the retinal surface. Such cutting instruments are also objectionable since they place added traction on the vitreoretinal membrane at the point of attachment to the retina as a result of shear during the cutting operation. Accordingly, there is a propensity of retinal tears and hemorrhage during such mechanical cutting.

Another disadvantage of the trans pars plana and transcorneal approaches using mechanical cutters is the inability to control hemorrhage within the vitreous cavity. This deficiency is especially complicated in the case of damaged or leaking vessels of diabetic patients. It is well established that vitreous hemorrhage is a frequent complication of diabetic retinopathy and retinal detachment. Once vitreous hemorrhage has occurred, adhesions develop between the retina and the vitreous body. These adhesions form adhesive bands similar to scars which tend to contract and cause traction on neighboring retinal blood vessels and the retinal tissue itself. The consequence is subsequent vitreous hemorrhage and retinal detachments frequently leading to complete blindness.

The pars plana incision requires viewing of the procedure using an operating microscope positioned above the eye and through a corneal contact lens. Accordingly, there is loss of visibility of the cutting instrument as it approaches the posterior region of the vitreous cavity in a case of massive vitreous hemorrhage. Moreover, if a cataract is present, viewing is impaired.

This deficiency in prior art vitreous procedures becomes further complicated when the hemorrhage may be so dense that the surgeon cannot adequately differentiate a neovascularized vitreoretinal membrane from retinal tissue with its normal vascular supply. Internal illumination by means of fiber optics has generally been developed; however, there is no instrument which currently allows a surgeon to view as well as illuminate the operative site from within the vitreous cavity. Accordingly, while significant advances have occurred in vitreous surgery, significant problems remain.

In response to these problems, the use of a $CO_2$ laser for simultaneously accomplishing both photo-transection and photocoagulation has been proposed as a cutting tool. A second unique advantage of a $CO_2$ laser operating at 10.6 μm is its absorption by almost all biological tissue at the point of contact. While this characteristic may be a deficiency in other procedures, it is a material advantage in vitreous surgery since little damage to neighboring or remote ocular tissue occurs. The propensity for damage to retinal tissue is minimized. The problem of propagation through the vitreous cavity, striking the optic nerve is eliminated. Fine et al, in "Preliminary Observations on Ocular Effects of High-Power, Continuous $CO_2$ Laser Irradiation", Am. J. Ophth. 64:209, August 1967 report that utilizing $CO_2$ laser radiation on the cornea resulted in little effect on underlying ocular structures. Data By Karlin et al in "CO2 Laser in Vitreoretinal Surgery", Ophthamology 86:290, February 1979 indicates that the depth of penetration of 10.6 μm radiation is about 10 microns. This minimal depth of penetration is in direct contrast to laser radiation occurring in the visible spectrum, for example, in argon and ruby lasers where propagation occurs through the vitreous over long distances potentially damaging the retina and the optic nerve. Given the high absorption at the point of contact, the CO2 laser beam can therefore be used to achieve simultaneous cutting and coagulation while other types of lasers cannot. In vitreous surgery, this advantage minimizes the possibility of hemorrhage when neovascular membranes are severed, a problem common in current mechanical cutters.

Investigations have already attempted to determine the feasibility of utilizing a CO2 laser in vitreoretinal surgery. One report, Karlin et al, supra. investigates four potential applications of this technology. These applications include photo-transection and photocoagulation, intravitreal biopsy, full thickness sclera-chorioretinal wall resection and, radiation effects on the lens. Other reports in the literature such as Campbell et al, "Laser Photocoagulation of the Retina", Tr. Am. Acad. Ophth. Otolaryng. 70:939, November–December 1966; Miller et al, "Transvitreal Carbon Dioxide Laser Photocautery and Vitrectomy", Tr. Am. Acad. Ophth. Otolaryng. 85:1195, November 1978 indicate that evaluation of CO2 lasers for vitreal surgery have taken place. To date, however, those reports and experiments have been done utilizing rudimentary instruments primarily concerned only with investigating photo-transection and photocauterization. The development of a CO2 laser instrument capable of widespread ophthalmic clinical use has yet to be achieved.

The definition of such an instrument requires a careful matching of surgical requirements with the level of engineering and scientific knowledge necessary to actually build the device. Hence while the surgeon can define his goals, the level of engineering know-how has not to date been sufficient to achieve them. Laser power requirements, precise focus, minimum instrument size, levels of illumination and field of view angles are all problems that remain.

The prior art is also replete with patents describing laser instruments that conceptually find utility for eye surgery. One, L'Esperance, Jr., U.S. Pat. No. 3,982,541 relates to the use of a CO2 laser probe coupled to a laser source by means of articulated couplings. One probe configuration utilizes a series of circumferential segmented chambers for the introduction of a stabilizing fluid to maintain eye inflation, that is, an irrigation channel, and an aspiration channel to evacuate debris. The probe size is unacceptably large.

This patent perceives that a fiber optic bundle can be utilized in place of the articulated segments each having mirror elements, given the propagation losses in such articulated arms. However, in such a case, the CO2 laser cannot be utilized and the patent affirmatively recognizes that some other type, such as argon, should be utilized. Accordingly, the U.S. Pat. No. 3,982,541 patent perceives the difficulties of transmitting CO2 10.6 μm radiation through fiber bundles.

U.S. Pat. No. 4,122,853 also relates to laser photocautery for use in vitreous surgery. A CO2 laser is utilized in combination with an articulated arm having mirrored joints. The probe is inserted in the pars plana region to a depth where the tip contacts the vascular tissue to be cauterized. A number of probe embodiments are shown, with the embodiments shown in FIGS. 9–11 of the U.S. Pat. No. 4,122,853 patent having a laser light guide tube 34, an irrigation channel 45, an aspiration channel 78, and, an illuminating light conduit 44. The particular embodiment shown in FIGS. 9–11 of the U.S. Pat. No. 4,122,583 patent does not provide for fiber optic viewing. However, this patent in FIG. 4 perceives an endoscope-like embodiment utilizing simultaneous illumination and viewing. Moreover, while five functions are shown in the various probe configurations of the U.S. Pat. No. 4,122,583 reference, they are not combined into a single functional unit.

An important criterion for probe configuration is to reduce the size to minimize trauma to the eye occasioned by large incisions. The probe should also match the geometry of the incision. Probes having a gauge greater than an 18–20 gauge hypodermic needle are considered unsuitable for vitreous procedures. Given this requirement for minimization of cross-sectional size, the optimization of the probe presents one area of continuing research. If the cross-sectional size is decreased, it becomes increasingly difficult to provide adequate illumination at the probe end. Problems of cold light and laser beam attenuation become significant and, when coupled with insufficient resolving power in the optic viewing segment tend to render those combined features unworkable. Such problems are compounded in the case of procedures within the vitreous cavity where the field of view is frequently clouded by hemorrhage.

Another problem not adequately addressed in prior art systems is the power loss attendant to transmission of the laser beam from the laser to the probe. This problem is particularly acute in the case of CO2 lasers where absorption occurs at the point of contact. Hence, special arrangements are necessary to transmit a CO2 laser beam along an irregular path.

U.S. Pat. No. 4,170,997, is directed to this problem and relates to a laser for surgical applications and specifically, a CO or a CO2 laser having illumination through fiber bundle 13 and viewing through fiber optic bundle 16. An axial hollow tube 18 contains a flexible infrared transmitting fiber optical waveguide 19 coupled to a laser source 20. An aiming or target beam produced by HeNe laser is utilized with transmission selectively coupled by means of an optical shutter 22 interposed in the path of the CO2 laser beam.

An important problem in the delivery of infrared laser radiation is the provision of a flexible radiation path between the laser source and the non-fixed probe. In the prior art, a number of solutions have been suggested. Among them are conventional articulating arms, as in U.S. Pat. No. 4,122,853 and illustrated in Herriott, "Application of Laser Light", Scientific American, 219, 144 (1968); flexible metal waveguides in Garmire et al, "Low Loss Propagation and Polarization Rotation in Twisted Infrared Metal Waveguides", Appl. Phys. Letters 34(1), 35 (1979); and infrared transmitting fibers in Pinnow, U.S. Pat. No. 4,170,997; Pinnow et al, "Polycrystalline fiber Optical Waveguides for Infrared Transmission", Appl. Phys. Letters 33(1), 28 (1978); Bridges et al, "Single-Crystal AgBr Infrared Optical Fibers", Optics Letters 5, 85 (1980). These techniques all have serious difficulties.

In both metal waveguides and infrared fibers, as known in the art, the guides are multimode. The single mode radiation from the laser, when launched, rapidly degrades into a multimode pattern. The pattern changes in form and the beam wanders as the guide is moved to follow movements of the probe. Hence, the beam does not remain centered, a critical factor in ophthamalic surgery. Such degradation considerably reduces the maximum intensity that can be obtained by focusing the output radiation.

Prior art articulating arms while preserving the single mode suffer from alignment problems. Unless the input beam is precisely launched on axis and the arm mechanism is precisely correct, the output beam will wander in a complicated manner as the arm is manipulated. In the context of a surgical procedure this is unacceptable. Moreover, such arms have heretofore been large and cumbersome making them unsatisfactory linkages for hand-held probes.

SUMMARY OF THE INVENTION

Given the deficiencies in various prior art systems, the present invention provides a vitreous surgical system utilizing a single probe to introduce $CO_2$ laser energy directly into the vitreous cavity to accomplish photo-transection and produce photocoagulation. The probe also allows simultaneous illumination and viewing of the vitreous cavity using illumination within the eye. Irrigation and aspiration functions are also accomplished. Accordingly, a single, miniaturized, multi-function probe for intravitreal surgery is defined by the present invention.

This invention also incorporates a novel articulating arm using straight hollow dielectric waveguides of the Marcatili-Schmeltzer type. Such an arm is disclosed in co-pending application "Articulated Arm Radiation Guide" by T. J. Bridges and A. R. Strnad. Single mode propagation is maintained while arm size is reduced and precision assembly criteria are diminished. The transparent waveguide tube also acts as a light pipe to carry visible light from a source to the probe for internal illumination of the surgical site.

Accordingly, it is an object of the present invention to provide for an improved $CO_2$ laser system for use in vitreous surgery.

Another object of the present invention is to provide a laser surgical system incorporating simultaneous illumination and viewing of the vitreous cavity from within the eye.

A further object of the present invention is to provide for a single miniaturized multi-function probe for use in intravitreal surgery.

Yet another object of this invention is to provide for an improved surgical probe optimized to provide maximum functional operation within a probe of minimum size, thereby reducing the propensity of damaging ocular tissue.

Still another object of this invention is to define a $CO_2$ laser surgical system having an improved flexible radiation path coupling the energy source to the probe.

Additional objects, advantages and features of this invention will become apparent from the following detailed description of the preferred embodiment when considered in conjunction with the accompanying drawings. In the drawings, like reference numbers are utilized to identify the same parts throughout.

BRIEF DESCRIPTION OF THE DRAWINGS

FIG. 2 is an elevational view, partially cut-away, showing the laser delivery system including the articulated arm used in accordance with this invention;

FIG. 2A is a cut-away view showing operation of the mechanical shutter element;

FIG. 2B is a cut-away view showing the internal elements of the articulated arm including its coupling to the laser source;

FIG. 3 is an enlarged partial section of a laser coagulator probe in accordance with the present invention;

DESCRIPTION OF THE PREFERRED EMBODIMENT

Figure 1:
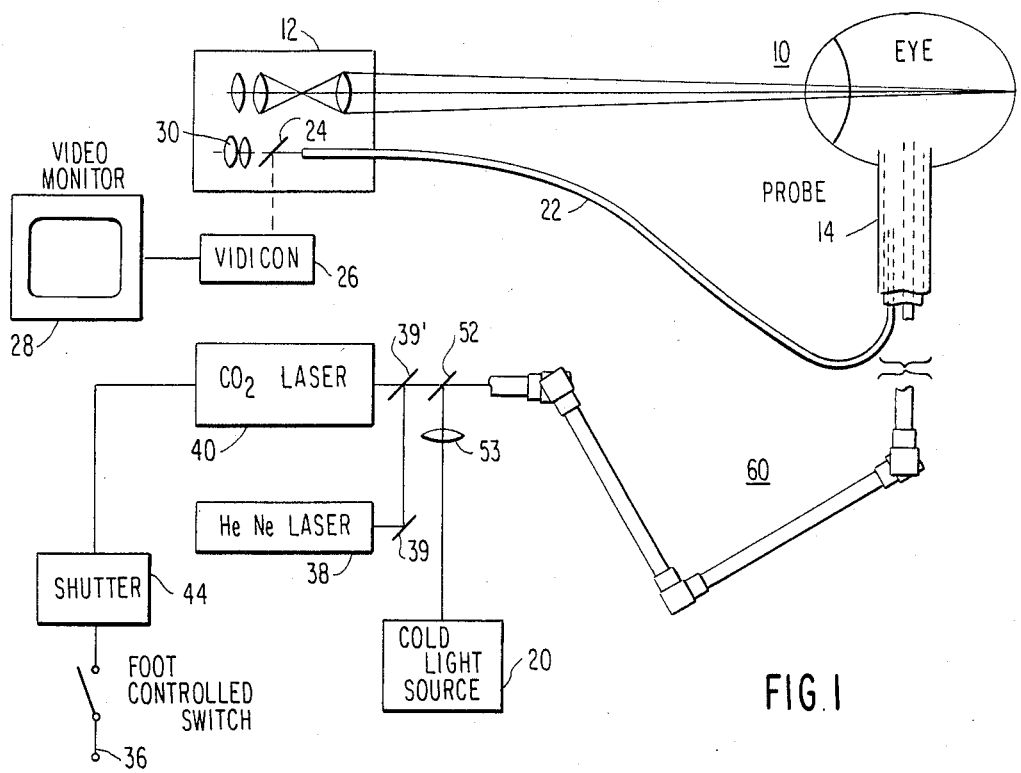
FIG. 1 is a block diagram of the multi-function laser vitrectomy system of this invention.

Referring now to FIG. 1, a schematic diagram of the $CO_2$ system in accordance with this invention is shown. FIG. 1 in schematic form shows the arrangement of the components utilized relative to a surgical procedure or an eye 10. In a conventional manner, the patient is positioned supine, with an operating microscope positioned directly above the face. The surgeon, working from behind and generally overhead, performs the microsurgery by viewing through the operating microscope 12. Such microscopes are well known in the technology and utilize foot pedals to operate focus and zoom controls allowing viewing of the vitreous through the iris of the eye 10. In accordance with one embodiment of the present invention, the operating microscope is also coupled to the probe 14 to allow direct viewing of the operative site from within the eye.

Figure 4:
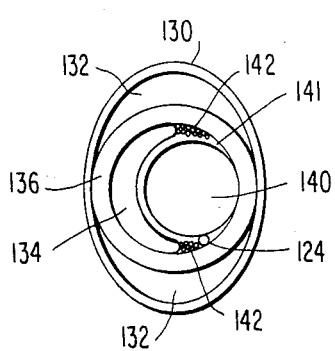
FIG. 4 is an enlarged end view of a probe including additional functions of aspiration, illumination, irrigation and internal viewing.
Figure 5:
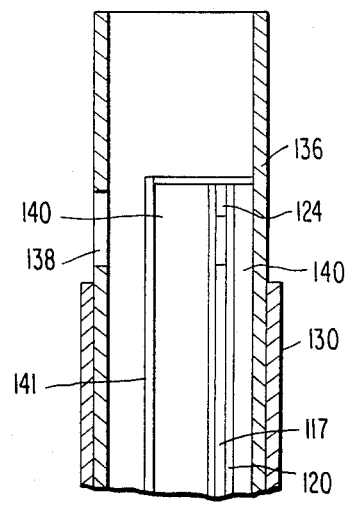
FIG. 5 is a section view of the probe of FIG. 4 for the multi-function vitreous probe.

The probe 14 is inserted into the vitreous cavity through an incision in the pars plana. One embodiment is shown in FIG. 3 for coagulation. The probe 14, to be described in detail with respect to the embodiment of FIGS. 4 and 5 is constructed utilizing a series of generally annular channels. The probe has preferably an elliptical shape.

Referring now to FIG. 2, a schematic diagram of the overall laser delivery system is shown. The primary laser power system forms a first major subsystem of this invention. A $CO_2$ laser, for example, a Sylvania Model 948, is shown schematically in FIGS. 1 and 2 as element 40. A laser attenuator 42, typically a Sylvania Model 485, is used to control the power over a range of 2-95% of laser output. The attenuator is adjustable by means of control knob 43. Power readout is by means of a readout module having a meter, now shown, and employs a power meter head 45 receiving the laser radiation beam 50 diverted from the radiation source 49 by mirror 44. As indicated in FIG. 2A, the laser radiation beam from the $CO_2$ laser is reflected by means of mirror 44 onto the power head 45 as a result of action of the mechanical shutter 46.

The mechanical shutter 46, typically a Uniblitz Model 114, when closed, reflects laser radiation via mirror 44 onto the power head 45. This allows a power output reading to be made. The shutter, when opened, transmits the laser beam to the delivery system. The shutter may be programmed to have an opening time in the range of 50 milliseconds to 100 seconds.

A focusing lens 47 is fixed on the threaded mount 47' shown in FIG. 2, to vary to focal length by rotational adjustment relative to block 47". The lens is typically made from zinc selenide material. The output, a focused beam, is then directed through a support tube 48 to the work illumination subsystem. The laser radiation beam passing through the opened shutter into and through the support tube 48 is shown as beam 51.

The work illumination system functions to inject visible light into the system for illumination of the surgical site. For this purpose, an ellipsoidal mirror 52 focuses incandescent light from a fiber optic light pipe into the fused quartz waveguide tube in the articulating arm structure to be discussed herein. An auxiliary focusing lens 53 receives light from a fiber optic light pipe 54. The light pipe is used in conjunction with a quartz halogen illuminator, not shown, to supply the visible light into the system. The auxiliary focusing lens 53 matches the light beam from the light pipe 54 into the ellipsoidal mirror 52. The mirror 52 has an opening to allow the laser beam to pass through into the articulating arm.

The articulating arm 60 is coupled to the work illumination system by means of a threaded ring disconnect 55. This disconnect mounting allows interchangeability of arms so that, for example, sterilization of individual elements can take place.

The articulating arm in accordance with the present invention solves a particularly crucial problem in the use of laser instruments for surgery by allowing single mode transmission, yet reducing in size prior art systems and eliminating beam wander as the arm is manipulated. The articulating arm comprises a series of straight precision bore quartz Marcatili-Schmeltzer waveguides which carry radiation in the hollow circular bore of a dielectric tube. The articulating arm 60, shown in FIG. 2B, comprises eight segments partially identified as 62, 64, 66, 68, and 70. In such systems, the dielectric need not be transparent to the radiation being guided. The mechanism of guiding through the waveguides can be considered as a continual glancing angle Fresnel reflection from the dielectric walls. While this reflection is not total, it is close to 100% for very shallow incident angles to the walls.

The modes of propagation of such waveguides have been calculated as for example in Marcatili et al, "Hollow Metallic and Dielectric Waveguides for Long Distance Optical Transmission and Lasers", Bell System Tech. J. 43, 1783 (1964). These waveguides are also described in detail in U.S. Pat. No. 3,386,043. As reported, the lowest loss mode is $EH_{11}$.

The approximate waveguide size is in the range of 50–200 wavelengths in diameter, this size being large enough to provide low loss, but still retain adequate guiding, so that straightness of the tube is not an important factor.

Because the dielectric need not be transparent to the radiation transported, glass or quartz tubing, readily obtainable in precision bore form, can be used to transport the 10.6 μm radiation. Single mode laser radiation is conveniently launched into the waveguide by means of the focusing lens 47. The focal length of the lens is chosen to closely match the Gaussian beam to the guided beam with small loss. This technique is described in Smith, "A Waveguide Gas Laser", Appl. Phys. Letters, 19, 132 (1971).

In such a system, small gaps in the waveguide tube are tolerated with minimal losses so that turning mirrors basic to the operation of the infrared articulating arm can be used in a simple arrangement. As shown in FIG. 2B, each link has an outer sheath 61 and is coupled to the succeeding link by means of swivel elbow members 72, 74, 76, 78, 80, and 82. The partial cutaway cross-section shows that each of the swivel elbows incorporates a 45° mirror 84 accurately fixed and mounted under a protective cap member 86. The dielectric waveguide, for example, those waveguides incorporated in members 62 and 64, protrude into the swivel elbow member 86. The dielectric waveguides are placed in close proximity to each other without actually contacting the mirror element 84. The mirror itself may be fabricated from silicon coated with silver and a transparent protective layer.

At each of the corners, swivelling is accomplished on precision ball-bearing mechanisms 88 and 90. If, for example, the total length of the articulated arm segments is in the range of 40 cm, the arm can then access any point in an 80 cm diameter sphere. Such an arm can have a transmission in the range of 80% and it has been demonstrated that a 1.55 mm diameter beam in the output tube will be transmitted in substantially single mode and focused to a near defraction limited spot.

In order to allow the transparent waveguide to act as a light pipe carrying visible light from the fiber optic light pipe 54, the mirror segments 84 should be highly reflecting in the visible as well as the infrared wavelengths. For this reason, evaporated silver is the coating material of choice. The light transmitted through the articulating arm illuminates the surgical work area or alternatively can be used for aiming the output beam.

The end of the articulating arm coupling it to the handle portion 91 has a threaded disconnect section 92 similar in construction to threaded disconnect section 55. As shown in FIG. 2B, the disconnect section 55 has an outer threaded ring 94 having threads compatible with the inner surface 96. A short waveguide tube section 98 provides a transition guide portion between the ellipsoidal mirror 52 and the articulating arm segments. A second waveguide section 100 projects into near abutment with waveguide section 98. Waveguide 100 is fixedly mounted in an inner annular flange 102 coupled to the articulating arm. An outer annular flange 104 projects from the coupling region so that by means of bearings 106, 108 the waveguide sections 98 and 100 may be accurately axially placed relative to each other yet rotation between the coupled segments may exist given the bearing coupling 106, 108 while the units are connected or disconnected. The handle 90 may be connected or disconnected from the articulating arm by means of a similar threaded ring coupling.

Referring to FIGS. 2 and 3, one embodiment of the delivery probe in accordance with the present invention is shown. The probe of FIGS. 2 and 3 is used for $CO_2$ laser coagulation and cutting incorporating the transmission of visible light for illumination of the surgical area. A fused quartz waveguide 110 is provided with a taper section 112. Typically, the waveguide may have a straight section of 1.5 mm ID, matching that of the articulating arm followed by a section tapering down to 0.5 mm. The straight section may be in the order of 96 mm long followed by a 23 mm tapered section. A liner 114 is used to house and provide longitudinal strength for the straight and tapered waveguide sections.

The probe section 116 comprises two sections 118 and 120. Section 118 is fashioned from stainless steel and the outer section 120 from silver. An anti-corrosion interface is provided on the outer section and the two elements are soldered together and to the ferrel 122. A fused quartz waveguide 117 in the order of 30 mm long of an internal diameter of 0.8 mm is provided inside the tube probe sections.

The composite probe tip utilizes a polished diamond window 124. A Type IIa diamond provides high transmission of $CO_2$ laser radiation together with high thermal conductivity. The diamond surface remains unaffected by high power densities of radiation and by burning or evaporating the body tissue which it comes in contact with. Accordingly, burn-on layers of material are easily removed by scraping without actually damaging the diamond window. the window 124 is soldered to the silver probe tip 120 with silver bromide, a highly insoluble non-toxic material.

The handle section 90 has a roughened outer surface 91 to provide for positive contact with the surgeon's hand. The ferrel 122 unscrews from the handle 90 to allow probe tips to be interchanged. An O-ring 126 is used to hermetically seal the probe-handle joint.

The waveguide taper in section 112 serves to reduce the overall cross-section of the waveguide from the 1.5 mm ID to a size compatible with the internal fused waveguide in the probe tip. At the same time, the taper concentrates the 10.6 $\mu$m wavelength $CO_2$ laser radiation into the probe tip. The sheath portion of the waveguide sections 110 and 112 acts as a carrier for illuminating light into the probe.

Given this description of the first preferred embodiment of this invention, as shown in FIG. 1, the probe which may either be elliptically shaped or circularly shaped as is the probe 116 is inserted into the eye in the manner herein disclosed. A foot controlled switch 36 is used to actuate the shutter mechanism 46. When closed, reflected laser radiation via mirror 44 is directed to the power meter head 45 for a readout on an auxiliary power meter. In the open position, laser light is transmitted to the delivery system.

A low power visible aiming laser beam 38, typically a HeNe laser, may also be employed with the $CO_2$ laser to provide an aiming beam in the form of a small spot at the focus of the final lens. This aiming beam supplants the visible light source which is too diffuse for an aiming operation. The spot is used to aid the surgeon in determining, with a high degree of precision, the exact point where photo-transection will take place. The HeNe laser is normally "on" as is the visible light source to additionally provide the surgeon with an indication of the orientation of the probe, vis-a-vis the site of interest in the vitreous cavity. The emission from the helium neon laser 38 may be introduced into the delivery system in a manner compatible with the work illumination system shown in FIG. 2. Beam splitters 39 and 39' may be used to introduce the HeNe radiation into the exit port of the illumination subsystem.

Referring now to FIGS. 4 and 5, a second probe system is shown. The probe 130 is elliptical having an irrigation channel 132 disposed in crescent-like segments inside the elliptical shell. An aspiration channel 134 is defined by the inner sheath 136 separating the irrigation channel 132 from the aspiration channel 134. Although aspiration occurs from the tip end of the probe, an aspiration hole 138 may be provided in the sidewall of the sheath. Also, if desired, a mouth, not shown in FIG. 5, may be formed by a projection of the circular sheath 136 extending axially beyond the end of the probe.

A viewing lens 140 is positioned eccentrically within the sheath 130 and maintained in place in a water-tight manner relative to the aspiration channel by means of the packing 141. The distal end of the probe containing the infrared waveguide terminates in the diamond mirror section 124. The size of the mirror section 124 is reduced vis-a-vis the FIG. 3 probe. As shown in FIG. 5, the outer probe section 120 projects asymmetrically adjacent to the viewing lens 140 and terminates with the diamond window 124.

In accordance with the embodiment of FIGS. 4 and 5, the irrigation and aspiration functions exit the probe 116 at a point before it reaches the ferrel 122. Coupling of those functions to the required sources of vacuum and fluid supply are done in a manner well established in the art. Hence, the probe may be used for photocoagulation and photo-transection as well as in vitreous transplantation surgery.

An important aspect of the embodiment of FIGS. 4 and 5 is the ability to illuminate and view the surgical site internally. In that regard, the viewing lens 140 may preferably utilize a SELFOC ® lens manufactured by Nippon Sheet Glass Co. Such lenses form an inverted real image of the object plane at the end of the viewing fiber bundle containing in the order of 30,000 optical fibers, each of 10 $\mu$m diameter. This would correspond to approximately 100 lines/mm of resolution. Focusing of different object planes onto the fiber bundle is accomplished by sliding the fiber bundle utilizing an adjustment at the instrument handle end. The adjustment varies the spacing of the fiber optic bundle relative to the viewing lens 140. Hence, focusing is achieved by varying the distance between the image plane and the viewing lens. the inverted image formed at that plane, inverted in the external eyepiece at the microscope thereby produces an upright image for use by the surgeon using lens system 30 shown in FIG. 1.

As shown in FIG. 1, the output of the viewing fiber bundle 22 may be transmitted to a vidicon camera 26 by means of beam splitter 24. This technique allows viewing of the surgical area on a video monitor 28. If necessary, the entire procedure can be recorded utilizing the vidicon output on magnetic tape. Moreover, given the inherent electronic flexibility provided by video recording, it is possible to correct, enhance, and magnify any portion of the area being viewed to discern appropriate detail that would be generally lost.

In accordance with this invention, the illumination of the surgical area is accomplished by light from the visible light source propagating down the same waveguide system used to transport the $CO_2$ laser beam. In the probe of FIG. 5, fibers 142 may be used to provide light at two locations circumferentially spaced about viewing lens 140. Hence, illumination takes place at the exact location of interest at the same time viewing takes place, utilizing the viewing bundle 142 positioned relative to the viewing lens 140 in the probe end. Since the viewing bundle 142 is typically made up utilizing quartz fibers, not transmitting $CO_2$ laser radiation, there is no possibility of injury to the viewer's eye when looking directly at the operating area through the microscope.

Accordingly, given the inherent flexibility of the system shown in FIGS. 4 and 5, the surgical procedure is expedited. The surgeon can continuously view, photo-transect, reposition, without moving away from the operating microscope.

In accordance with this invention, 10.6 $\mu$m $CO_2$ radiation is effectively transmitted without power loss and without beam wander. Because different techniques place different requirements on the system, the achievement of these two capabilities is significant. For example, photocoagulation places a power requirement on the system and the ability to tranmsit through the articulating arm into the probe section without significant power loss becomes important. Power up to 5 cw has been transmitted without damage to the system. However, photo-transection places a different requirement on the system, namely, intensity (power/unit area). Given the fact that the present invention allows for single mode delivery, surgically clean transection of ocular tissue can take place. Therefore, the present invention represents a significant improvement over prior art systems by providing a highly focused intense beam at the surgical site.

It is appreciated that modifications of this invention may be achieved without departing from the essential scope thereof.

Having described our invention, we claim:

1. A surgical instrument for treating biological tissue comprising:
   a $CO_2$ laser power source producing a single mode laser beam;
   an articulated arm coupled to said $CO_2$ laser source comprising a series of coupled rigid straight hollow dielectric waveguides joined by elbow corner mirrors therein, said articulated arm transporting said single mode laser beam without mode conversion; and
   a probe coupled to said articulated arm receiving said single mode laser beam and directing said beam onto portions of biological tissue to be treated.

2. A surgical instrument for photo-transection or photocauterization of tissue comprising:
   a $CO_2$ laser power source producing a single mode radiation laser beam;
   an articulated arm coupled to said laser source and comprising a series of coupled rigid straight hollow dielectric waveguides maintaining single mode radiation of said laser beam; and
   an output probe coupled to said articulated arm and adapted to focus said laser beam to portions of tissue for treatment.

3. The instrument of claim 1 or 2 further comprising means to attenuate the output power of said laser beam prior to launching in said articulated arm.

4. The instrument of claim 1 or 2 further comprising shutter means selectively actuated to divert said laser beam off a launching axis into said articulated arm to a second axis of propagation, and means positioned relative to said second axis of propagation to measure the power of said diverted laser beam.

5. The instrument of claim 1 or 2 further comprising a source of visible light, and means to introduce said visible light into said articulated arm.

6. The instrument of claim 5 wherein said laser beam is launched into said articulated arm along a launching axis centered with the central longitudinal axis of a first of said straight hollow dielectric waveguides, an allipsoidal mirror positioned on said launching axis and having an opening to allow said laser beam to pass therethrough, said ellipsoidal mirror focusing visible light from said source onto an end of said first of said hollow dielectric waveguides.

7. The instrument of claim 6 wherein said dielectric waveguides are Marcatili-Schmeltzer waveguides that transport said laser beam internally and propagate said visible light through the waveguides themselves.

8. The instrument of claim 1 or 2 further comprising means to disconnect said articulated arm from said laser power souce.

9. The instrument of claim 8 further comprising means to disconnect said probe from said articulated arm.

10. The instrument of claim 1 or 2 wherein said probe comprises a probe tip having a hollow waveguide member therein of smaller internal cross-section area than said waveguides in said articulated arm, a window at one end of said probe tip, and a waveguide within said probe having a tapered section optically coupling the other end of said probe tip to a junction point with said articulated arm.

11. The instrument of claim 10 wherein said probe tip comprises a first section formed from a high stength material and a second section formed from a corrosion resistant material, said first and second sections joined together in axial alignment.

12. The instrument of claim 1 or 2 further comprising means defining an aspiration source, said probe having an axial aspiration channel coupled to said aspiration source, means defining a fluid source and an irrigation channel in said probe coupled to said fluid source.

13. The instrument of claim 12 further comprising a viewing lens positioned in said probe, a fiber optic bundle disposed in said probe having an end in a spaced relationship from said viewing lens and, means to display an image focused on said end of said fiber optical bundle by said viewing lens.

14. The instrument of claim 13 wherein said means to display comprises a surgical microscope.

15. The instrument of claim 13 wherein said means to display comprises a vidicon coupled to said fiber optic bundle and, a cathode ray tube coupled to said vidicon.

16. The instrument of claim 1 or 2 further comprising a second laser source, said second laser source producing a low power visible laser beam and means to introduce said visible laser beam into said articulated arm.

17. The instrument of claim 1 further comprising a viewing lens positioned in said probe, a fiber optic bundle disposed in said probe having an end in a spaced relationship from said viewing lens and, means to display an image focused on said end of said fiber optic bundle by said viewing lens.

18. A surgical method for vitreous surgery comprising the steps of providing a $CO_2$ laser source producing a single mode 10.6 $\mu$m beam;
   transporting said beam through an articulated arm comprising a series of connected straight hollow dielectric waveguides for transporting said beam without mode conversion; and
   focusing said transported beam in a probe having a portion introduced into the vitreous cavity, and performing the surgical procedure with said focused beam.

19. The method of claim 18 wherein said surgical procedure is photo-transection of vitreoretinal scar tissue.

20. The method of claim 18 wherein said surgical procedure is selected from the group consisting of photo-coagulation of retinal tears, hemorrhaging retinal vessels and hemorrhaging neovascular vitreoretinal membranes.

21. The method of claim 19 further comprising the step of aspirating the vitreous tissue and/or material that has been photo-transected.

22. The method of claim 19 or 20 further comprising the step of irrigation of the surgical site during said surgical procedure.

23. The method of claim 18 19 or 20 further comprising the steps of illuminating the surgical site by introduction of visible light into the vitreous cavity from said probe and viewing the surgical site from within said vitreous cavity.

24. A surgical instrument for treating biological tissue comprising:
a $CO_2$ laser power source producing a single mode laser beam;
an articulated arm coupled to said $CO_2$ laser source comprising a series of coupled rigid straight hollow dielectric waveguides joined by elbow corner mirrors therein, said articulated arm transporting said single mode laser beam without mode conversion; and
a probe coupled to said articulated arm receiving said single mode laser beam and directing said beam onto portions of biological tissue to be treated, and comprising a probe tip having a hollow waveguide member therein of smaller internal cross-section areas than said waveguides in said articulated arm, a window at one end of said probe tip, and a hollow waveguide within said probe having a tapered section optically coupling the other end of said probe tip to a junction point with said articulated arm, wherein said tapered section reduces in internal hollow cross-section to less than the internal hollow cross-section of said probe tip waveguide member to focus and to transport said laser beam into said probe tip and said tapered section maintaining a constant external size to define a sheath interface with said waveguide member for propagation of visible light.

25. A surgical instrument for photo-transection or photocauterization of tissue comprising;
a $CO_2$ laser source producing a single mode radiation laser beam;
an articulated arm coupled to said laser source and comprising a series of coupled rigid straight hollow dielectric waveguides maintaining single mode radiation of said laser beam; and
an output probe coupled to said articulated arm and adapted to focus said laser beam to portions of tissue for treatment, and comprising a probe tip having a hollow waveguide member therein of smaller internal cross-section area than said waveguides in said articulated arm, a window at one end of said probe tip, and a hollow waveguide within said probe having a tapered section optically coupling the other end of said probe tip to a junction point with said articulated arm, wherein said tapered section reduces in internal hollow cross-section to less than the internal hollow cross-section of said probe tip waveguide member to focus and to transport said laser beam into said probe tip and said tapered section maintaining a constant external size to define a sheath interface with said waveguide member for propagation of visible light.

* * * * *

UNITED STATES PATENT AND TRADEMARK OFFICE
CERTIFICATE OF CORRECTION

PATENT NO. : 4,583,539
DATED : April 22, 1986
INVENTOR(S) : David B. KARLIN et al It is certified that error appears in the above-identified patent and that said Letters Patent is hereby corrected as shown below:

Column 1, line 2, following title, insert as a new paragraph:

-- This invention was made under a U.S. Government Grant EY02410-03. --

Signed and Sealed this

Fourth Day of November, 1986

[SEAL]

*Attest:*

DONALD J. QUIGG

*Attesting Officer*     Commissioner of Patents and Trademarks